(12) United States Patent
West et al.

(10) Patent No.: US 8,329,397 B2
(45) Date of Patent: Dec. 11, 2012

(54) CHEMILUMINESCENCE PROXIMITY NUCLEIC ACID ASSAY

(75) Inventors: Anthony West, Denver, CO (US); Millard Gambrell Cull, Brighton, CO (US)

(73) Assignee: Beacon Biotechnology Inc., Aurora, CO (US)

( * ) Notice: Subject to any disclaimer, the term of this patent is extended or adjusted under 35 U.S.C. 154(b) by 0 days.

(21) Appl. No.: 11/448,167

(22) Filed: Jun. 5, 2006

(65) Prior Publication Data

US 2010/0221703 A1 Sep. 2, 2010

Related U.S. Application Data

(60) Provisional application No. 60/687,647, filed on Jun. 3, 2005.

(51) Int. Cl.
| | |
|---|---|
| C12Q 1/68 | (2006.01) |
| C12Q 1/66 | (2006.01) |
| G01N 33/53 | (2006.01) |
| G01N 21/76 | (2006.01) |
| C12M 3/00 | (2006.01) |
| C07H 21/02 | (2006.01) |
| C07H 21/04 | (2006.01) |

(52) U.S. Cl. .......... 435/6.1; 435/7.1; 435/8; 435/287.2; 436/172; 436/501; 536/23.1; 536/24.1

(58) Field of Classification Search .......... 435/6.1, 435/7.1, 8, 287.2; 436/172, 501; 536/23.1, 536/24.1
See application file for complete search history.

(56) References Cited

U.S. PATENT DOCUMENTS

| | | | |
|---|---|---|---|
| 4,687,636 A | | 8/1987 | Hart |
| 4,794,073 A | | 12/1988 | Dattagupta et al. |
| 5,340,716 A | | 8/1994 | Ullman et al. |
| 5,660,993 A | | 8/1997 | Cathey et al. |
| 5,804,380 A | | 9/1998 | Harley et al. |
| 5,837,465 A | * | 11/1998 | Squirrell et al. .......... 435/6 |
| 5,861,318 A | | 1/1999 | Elhammer |
| 5,891,639 A | | 4/1999 | Harley et al. |
| 6,113,886 A | | 9/2000 | Bryan |
| 6,232,107 B1 | | 5/2001 | Bryan et al. |
| 6,436,682 B1 | | 8/2002 | Bryan et al. |
| 6,444,476 B1 | | 9/2002 | Morgan |
| 6,465,182 B1 | | 10/2002 | Gray et al. |
| 6,544,746 B2 | | 4/2003 | Heyduk |
| 6,608,213 B1 | | 8/2003 | Sato et al. |
| 6,653,079 B2 | | 11/2003 | Yang et al. |
| 6,930,314 B2 | | 8/2005 | Jackson, III et al. |
| 7,041,451 B2 | | 5/2006 | Zhang et al. |
| 7,247,443 B2 | | 7/2007 | Su |
| 2003/0203404 A1 | | 10/2003 | Joly |
| 2004/0063147 A1 | * | 4/2004 | Natrajan et al. .......... 435/7.1 |
| 2004/0214227 A1 | | 10/2004 | Joly |
| 2006/0099646 A1 | | 5/2006 | Heding |

FOREIGN PATENT DOCUMENTS

WO    WO 03/102239    * 12/2003

OTHER PUBLICATIONS

Kleinjung et al., 1997, Anal. Chimica Acta 350: 51-58.*
Verhaegen et al., 2002, Anal. Chem. 74: 4378-4385.*
Schuderer et al., 2000, Anal. Chem 350: 3942-3948.*
Yamakawa et al., 2002, J of Bioscience and Bioengineering 93: 537-542.*
Cardullo et al., 1988, PNAS 85: 8790-8794.*
Tannous et al., Molecular Therapy 11: 435-443.*
Okamura et al, Double labeled donor probe can enhance the signal of FRET in detection of nucleic acid hybridization, 2000, Nucleic Acids Research, 28, e107, pp. 1-6.*
Szent-Gyorgyi et al, cloning and chracterization of new bioluminescent protein, 2003, procceding of SPIE, nanolight section.*
Szent-Gyorgi et al publication date confirmation brochure, printed Nov. 10, 2009.*
Seville et al (Oct. 21, 1996) Biotechniques (4) : 664, 666, 668, 670, 672, Fluorometric assay for DNA polymerases and reverse transcriptase.
Alba et al. (Apr. 1999) Photochemistry and Photobiology, 69(4):405-409, "Inhibition of peroxyoxalate chemiluminescence by intercalation of fluorescent acceptors between DNA bases".
Alba et al (May 2001) Luminescence 16(3):247-249, "Detection of Texas red-labeled double-stranded DNA by non-enzymatic peroxyoxalate chemiluminescence".

* cited by examiner

*Primary Examiner* — Stephen Kapushoc
*Assistant Examiner* — Narayan Bhat
(74) *Attorney, Agent, or Firm* — Swanson & Bratschun, LLC

(57) ABSTRACT

This invention relates to the detection and quantitation of target nucleic acids in a heterogeneous mixture in a Sample and the methods of use thereof. The detection system includes a chemiluminescent molecule, a chemiluminescent substrate, a dye that is light responsive when intercalated into nucleic acids and nucleic acids. This invention is useful in any application where detection of a specific nucleic acid sequence is desirable, or where the detection of enzymes that modify nucleic acids is desirable such as diagnostics, research uses and industrial applications.

14 Claims, 8 Drawing Sheets

A.

B.

A.

B.

C.

CHEMILUMINESCENCE PROXIMITY NUCLEIC ACID ASSAY

CROSS-REFERENCE TO RELATED APPLICATIONS

The subject application claims the benefit of priority to U.S. Application Ser. No. 60/687,647, filed on Jun. 3, 2005, which is incorporated by reference herein in its entirety.

FIELD OF THE INVENTION

This invention relates to the detection and quantitation of target nucleic acids in a heterogeneous mixture in a Sample and the methods of use thereof. The detection system includes a chemiluminescent molecule, a chemiluminescent substrate, a dye that is light responsive when intercalated into nucleic acid and a nucleic acid target. The method requires that a specific three-dimensional structure (i.e. Dye intercalated into nucleic acid) be created for energy to be accepted by the dye and that the energy donor (Chemiluminescent Molecule) be proximal to this structure. This invention is useful in any application where detection of a specific nucleic acid sequence is desirable, or where the detection of enzymes that modify nucleic acids is desirable such as diagnostics, research uses and industrial applications.

BACKGROUND OF THE INVENTION

Nucleic acids are measured to identify molecules of a specific target nucleic acid sequence in a population of heterogeneous nucleic acids, DNA or RNA, or to measure products of reactions where nucleic acids, DNA or RNA, are modified. Such measurements are generally permutations of the following procedures:

a. where the starting nucleic acid is RNA, conversion to DNA is accomplished by a reverse transcription reaction. The oligonucleotide primers for the reverse transcription reaction may be specific for the target sequence or may be general for conversion of all RNA sequences to DNA;

b. amplification of the target nucleic acid by target sequence specific reactions. These include polymerase chain reaction (PCR) with sequence specific primers, and primer extension reactions again with a target sequence specific oligonucleotide primer. Rolling circle amplification of DNA has also been used to amplify specific DNA sequences;

c. physical separation of the heterogeneous nucleic acids. Such physical separations include but are not limited to size fractionation and affinity separation when amplified nucleic acids are produced with derivatized substrates including but not limited to biotinylated deoxyribonucleotide triphosphates;

d. labeling of the nucleic acid. As mentioned in c. above, amplified nucleic acids may be labeled using either derivatized deoxyribonucleotide triphosphates or derivatized oligonucleotide (RNA or DNA) primers; and e. detection of the nucleic acids. Nucleic acids can be detected either through the labeling moiety, or by physical separation followed by detection with nucleic acid specific dyes.

One of the more common methods for the quantitative detection of target sequences is the sequence specific amplification of the target sequence(s) by PCR, either from DNA or from cDNA after reverse transcription, physical separation by gel or capillary electrophoresis, and detection by fluorescent labeling (e.g. of dsDNA by ethidium bromide or by use of fluorescently labeled primers in the amplification). Another common technique for the quantitative detection of target sequence(s) involves "real time" PCR.

PCR technology is widely used to aid in quantitating DNA because the amplification of the target sequence allows for greater sensitivity of detection than could otherwise be achieved. The point at which the fluorescent signal is measured in order to calculate the initial template quantity can either be at the end of the reaction (endpoint QPCR) or while the amplification is still progressing (real-time QPCR). The more sensitive and reproducible method of real-time QPCR measures the fluorescence at each cycle as the amplification progresses.

The reporter molecule used in real-time QPCR reactions can be (1) a sequence-specific probe composed of an oligonucleotide labeled with a fluorescent dye plus a quencher or (2) a non specific DNA binding dye that fluoresces when bound to double stranded DNA.

Both of these techniques, and others not described in detail, require instrumentation either for physical separation or detection. The requirement for instrumentation and/or separation technologies with their attendant sample handling limits the use of quantitative and qualitative target sequence detection. Accordingly, there is a need for methods of detecting and measuring nucleic acids that do not require expensive, delicate instrumentation either for sample separation or for detection. Such measurements include but are not limited to the identification of molecules of a specific nucleic acid sequence as well as the detection of nucleic acids that are the product of nucleic acid modifying reactions. Nucleic acid modifying reactions include but are not limited to polymerization reactions, ligation reactions, nuclease reactions and recombination reactions.

Fluorescent Intercalating Nucleic Acid Dyes

A common method for the detection of nucleic acids is by staining them with fluorescing intercalating dyes. These dyes have several unique features that make them especially useful: 1) They have a high molar absorptivity; 2) Very low intrinsic fluorescence: 3) Large fluorescent enhancements upon binding to nucleic acids; and 4) Moderate to high affinity for nucleic acids, with little or no staining to other biopolymers. Intercalating nucleic acid stains have fluorescence excitations and emissions that span the visible-light spectrum from blue to near-infrared with additional absorption peaks in the UV, making them compatible with many different types of instrumentation. These dyes are excited with an extrinsic light source that has a spectrum that overlaps with the maximally excitation wavelength of the intercalated dye. They may be used to image both RNA and DNA. Some commonly used dyes are listed below.

| Dye Name | Ex/Em* | Application |
| --- | --- | --- |
| Ethidium Bromide | 300/600 | Quantitation and Detection of dsDNA |
| Ethidium Bromide | 510/620 | Quantitation and Detection of dsDNA |

-continued

| Dye Name | Ex/Em* | Application |
|---|---|---|
| Homodimer-1 | | |
| PICOGREEN ® Quantitation Reagent | 502/523 | dsDNA |
| OLIGREEN ® Quantitation Reagent | 498/518 | Quantitation and Detection of ssDNA and oligonucleotides |
| RIBOGREEN ® Quantitation Reagent | 500/520 | Quantitation and Detection of RNA |
| SYBR GOLD ® stain | 495/537 | Quantitation and Detection of single- or double-stranded DNA or RNA post-electrophoresis |
| SYBR GREEN I ® stain | 494/521 | Quantitation and Detection of double-stranded DNA and oligonucleotides post-electrophoresis Also useful for real-time PCR assays |
| SYBR GREEN ® stain | 492/513 | Sensitive stain for RNA and single-stranded DNA post-electrophoresis |
| SYBR SAFE ® stain | 502/530 | Sensitive DNA gel stain with significantly reduced mutagenicity |
| SYBR DX DNA BLOT ® stain | 475/499 | Sensitive stain for DNA |

*Excitation (Ex) and emission (Em) maxima are the wavelength, in nanometers, (nm) of light that maximally excites the intercalated dye and the wavelength of light that is maximally emitted when the dye fluoresces, respectively.

Resonance Energy Transfer

Energy may be donated to nucleic acid intercalated dye either by photons or by resonance energy transfer. The principle of energy transfer between two molecules can be exploited as a means to provide information about relative changes in their proximity and orientation to one another. Resonance Energy Transfer (RET) is the transfer of excited state energy from a donor to an acceptor molecule. Förster resonance energy transfer (FRET) is a distance-dependent interaction between the electronic excited states of two dye molecules in which excitation is transferred from a donor molecule to an acceptor molecule without emission of a photon. This can only occur if the absorption spectrum of acceptor molecule overlaps with the emission spectrum of the donor. Förster determined that the degree of resonance energy transfer between the energy donor and energy acceptor is inversely proportional to the distance between the two molecules to the sixth power. In the case of FRET, an external light source of specific wavelength is used to excite the donor molecule.

Bioluminescent Resonance Energy Transfer (BRET) uses biological molecules such as a luciferase as the donor molecule. Depending on the species of origin, luciferases that use coelenterazine as a substrate generate blue light in the range of 450 to 500 nm. When a suitable acceptor is in close proximity, the blue light energy is captured by RET. The acceptor molecules are generally a class of proteins that have evolved the ability to be excited by blue light and then fluoresce in longer wavelengths typically with maximal spectral emissions above 500 nm. In both FRET and BRET the molecules of interest may be either covalently or non-covalently linked or brought in to proximity by conformational change or by spatial migration or by an alteration in their relative orientations to one another. For instance, the two molecules may be conjugated to two separate proteins of interest. They may then be brought into proximity by their affinity for one another or their affinity for a third molecule. They may also be attached to a protein of interest and then brought closer due to a conformational change within the protein of interest. Generally the two molecules must be within 100 Å of one another for resonance energy transfer to occur and changes as little as 1-2 Å may be detected. Luciferases that have been used in BRET include those from the firefly, *Renilla reniformis* and *Gaussia princeps*. A commonly used fluorescent protein is the green fluorescent protein (GFP) from *Aequorea victoria*. BRET is generally used to measure the degree of affinity or degree of conformational change between two protein domains either covalently or non-covalently linked.

SUMMARY OF THE INVENTION

The present invention functions to bring a Chemiluminescent Molecule within close proximity to dye stained target nucleic acids or the products of nucleic acid modifying reactions. The ability of the energy to be accepted by the dye is conditional. It is necessary for the dye to be intercalated into nucleic acid and that the energy donor be in close proximity. The method requires that a specific three-dimensional structure (i.e. Dye intercalated into nucleic acid that is contacted to a Chemiluminescent Molecule) be created for energy to be accepted by the dye and that the energy donor be proximal to this structure.

Specific advantages of the present invention include the following. The invention is rapid, and does not require any wash steps, which is significant as would be recognized by one of skill in the art. It does not require radioactivity nor does it require a laser for activating nucleic acid conjugated fluorophores. The signal from the emitted light in the reactions may be integrated over minutes as opposed to milliseconds as is the case with laser activated fluorophores.

A unique aspect of this method is that of Proximity. Direct contact of the Chemiluminescent Molecule to the nucleic acid allows for the sensitive detection of a change in the mass of stainable nucleic acid (Example 3). The amount of fluorescence from nucleic acid that has been stained with an intercalating dye is directly proportional to the amount of nucleic acid present. Any condition in which the total mass of nucleic acid that is attached to the Chemiluminescent Molecule is increased or decreased will result in an increase or decrease of fluorescence by an activated intercalating dye.

The Chemiluminescent Molecule does not simply act as an indicator of the presence of contact of a probe to a fluorophore. It indicates that duplex nucleic acid is present by virtue of its illumination of dye bound that can only act as an energy acceptor when bound to duplex. In the case of detecting nucleic acids of specific sequence it adds a level of stringency.

A positive signal requires both that the indicator molecule (i.e. the Chemiluminescent Molecule) be associated with the target sequence and also that nucleic acid be present. In other words it demands that a specific three-dimensional structure be created for energy to be accepted by the dye and that the energy donor be a part and thus proximal to this structure. This will significantly reduce the background noise in the system for which it is being applied.

The presence of the target nucleic acid is conveyed when the light emitting Chemiluminescent Molecule is brought into close proximity in the presence of fluorescent intercalated dye. The light emitted by the intercalated dye is proportional to the amount of stainable nucleic acid that is in close proximity to the Chemiluminescent Molecule.

The present invention relates to a general detection system for nucleic acids and methods of use thereof. The preferred system comprises four reagents: 1) a Chemiluminescent Molecule, 2) a Chemiluminescent Substrate, 3) an Intercalating Dye and 4) Nucleic Acid. These reagents are contacted with a Sample and can detect a change in the mass of stainable nucleic acid caused hybridization to complementary nucleic acids or by nucleic acid modifying reactions. The nucleic acids in a Sample can be either unamplified or the result of amplification reactions.

A Chemiluminescent Probe may be made by covalently or non-covalently attaching the Chemiluminescent Molecule to a single stranded nucleic acid probe capable of hybridizing to complementary single stranded nucleic acid in the Sample. The target nucleic acid being probed in the Sample may be in solution phase with Chemiluminescent Probe in solution phase being added. The nucleic acid being probed in the Sample may be immobilized on a solid support with the Chemiluminescent Probe in solution phase being added. The Chemiluminescent Probe may be immobilized on a solid support with the nucleic acid being probed in the Sample in solution phase being added. The Chemiluminescent Probe and the nucleic acid being probed in the Sample may be immobilized.

The Intercalating Dye is added to the Sample containing double stranded nucleic acid and a Chemiluminescent Molecule or Probe and it intercalates into the double stranded nucleic acid regions in the Sample. The Chemiluminescent Substrate is added to the Sample and is activated by the Chemiluminescent Molecule. The interaction of the Chemiluminescent Molecule and Chemiluminescent Substrate produces energy that in turn excites the Intercalating Dye at the Intercalating Dye Excitation Wavelength and the Intercalating Dye emits light at the Intercalating Dye Emission Wavelength. The light emitted at the Intercalating Dye Emission Wavelength is measured (with or without appropriate emission filters) and it is possible to determine the presence and quantitate the amount of target nucleic acid in the Sample. Using a filter one may discriminate longer wavelength light emitted by the fluorescing intercalated dye from the shorter wavelength light emitted by the Chemiluminescent Molecule. This discrimination may also be accomplished by incorporating into the Chemiluminescent Reaction non-intercalating, non-fluorescing dyes that absorb light emitted at the wavelengths produced by the Chemiluminescent Molecule but not that of the fluorescent intercalated dye. This general method is depicted in FIG. 1.

In one non-limiting embodiment, the Sample contains single stranded genomic DNA suspected of containing integrated HIV proviral sequence. The Chemiluminescent Molecule is $Gaussia$ $princeps$ luciferase (gluc) and it is covalently attached to a ssDNA probe that is complementary to a region of the HIV envelope gene. The Intercalating Dye is PICOGREEN® quantitation reagent (formula: [2-[N-bis-(3-dimethylaminopropyl)-amino]-4-[2,3-dihydro-3-methyl-(benzo-1,3-thiazol-2-yl)-methylidene]-1-phenyl-quinolinium] and the Chemiluminescent Substrate is coelenterazine. The Sample DNA is denatured to generate single strands and then the probe covalently attached to $Gaussia$ luciferase is added to the Sample and hybridizes to its complement. The PICOGREEN® quantitation reagent is added to Sample and intercalates into the dsDNA region resulting from the probe hybridization. The coelenterazine is added to the Sample and causes the $Gaussia$ luciferase to emit blue light with a spectrum peak at 480 nm. The emitted blue light causes any intercalated PICOGREEN® quantitation reagent in close proximity to be excited, since its peak excitation wavelength is 502 nm. The PICOGREEN® quantitation reagent then emits a bright green spectrum of light with a peak at 523 nm that can be easily measured with a charged coupling device (CCD) camera that is equipped with a filter that significantly diminishes wavelengths below 500 nm.

An additional nonlimiting disclosure of the present invention would create a proximity assay by bringing a chemiluminescent molecule into close proximity with nucleic acid polymers incorporating fluorescently labeled nucleotides, or nucleotide analogs that fluoresce, in place of the intercalating dyes of the present invention. U.S. Pat. Nos. 6,451,536 and 6,960,436 describe the use of fluorescent nucleotides to detect and measure DNA samples without the component of proximity that embodies the present invention. These above referenced patents are hereby incorporated in their entirety by reference.

This invention is useful in any application where detection of the presence or absence of DNA is desirable, such as diagnostics, research uses and industrial applications. This method is particularly well suited to detecting DNA in Samples either in solution or in a microarray format. This method is also well suited to detecting the products of enzymatic activities that create or modify nucleic acid samples such as polymerases, nucleases, recombinases and ligases as well detecting inhibitors of these activities. The present invention also encompasses methods of use of the above-described system.

DETAILED DESCRIPTION OF THE INVENTION

Figure 1:
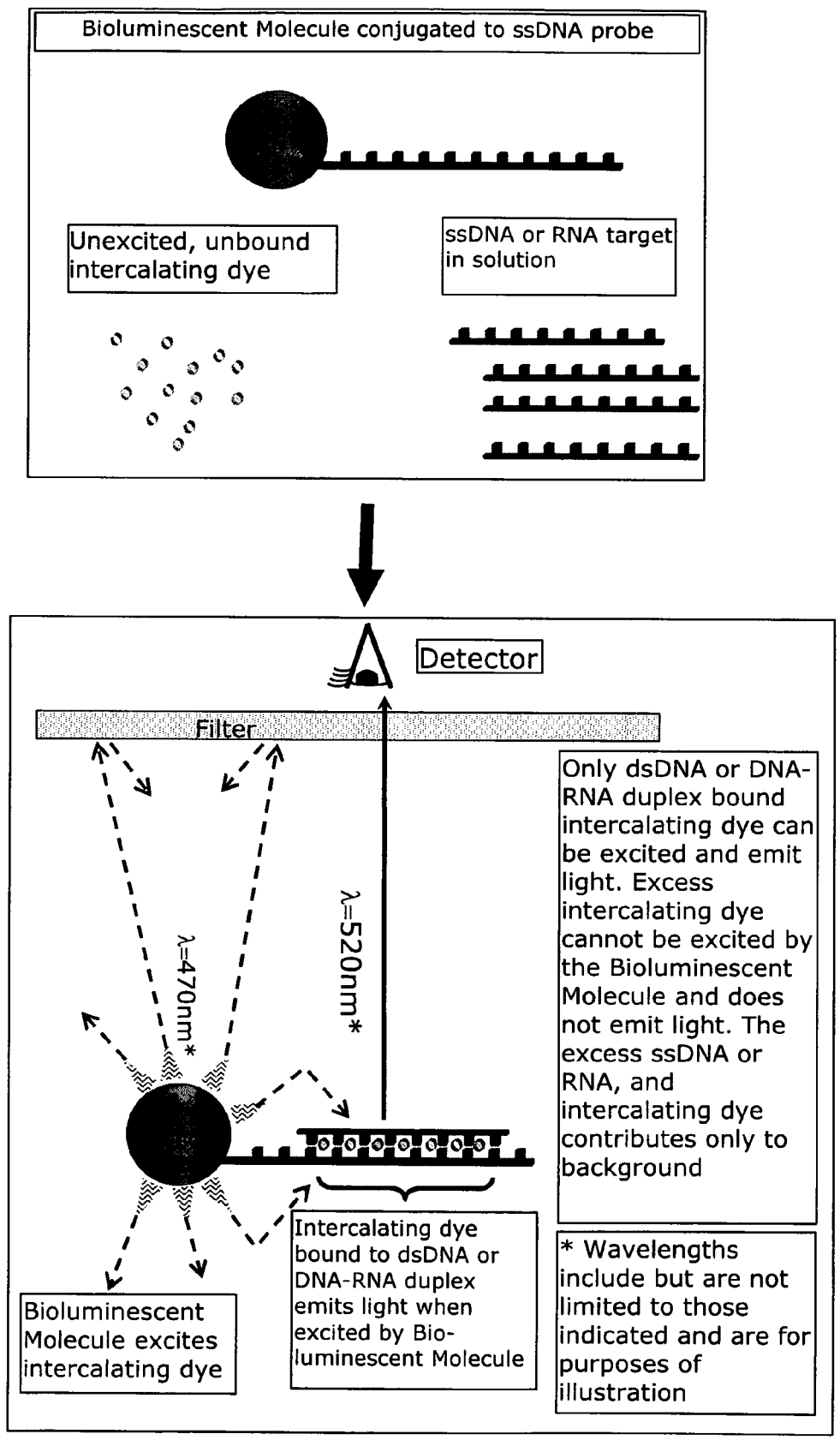
FIG. 1 depicts an embodiment having Probe directly attached to Chemiluminescent Molecule and Sample where both are unattached to a Solid Support.

The invention provides a general method for detecting the presence or absence of nucleic acid in a Sample. In a preferred embodiment, the system comprises four reagents: 1) a Chemiluminescent Molecule, 2) a Chemiluminescent Substrate, 3) an Intercalating Dye and 4) Nucleic Acids. The following terms are intended to have the following general meanings as they are used herein as would be readily understood by one of skill in the art.

A. Definitions

"Bioluminescent Molecule" means any biological molecule involved in a chemiluminescent reaction. The reaction may be either catalytic or stoichiometric.

"Chemiluminescent Emission Spectrum" means the range of photon wavelengths emitted by the Chemiluminescent Molecule. The spectrum is frequently defined by the wavelength of highest intensity from a chemiluminescent reaction.

"Chemiluminescent Probe" means an olio- or poly-nucleotide probe molecule with a coupled Chemiluminescent Molecule. The Chemiluminescent Molecule may be coupled covalently or through non-covalent interaction, either before or after modification of the Probe by target nucleic acid.

"Chemiluminescent Substrate" means a reactant that interacts with the Chemiluminescent Molecule to produce a photon/light.

"Chemiluminescent Molecule" means any molecule that takes part in any chemiluminescent reaction; this includes but is not limited to a bioluminescent molecule.

Various Chemiluminescent Molecules and their respective Chemiluminescent Substrates include but are not limited to:
  i) Luciferases that utilize coelenterazine as a Substrate including luciferases from the organisms *Gaussia princeps, Periphylla periphylla, Renilla mulleri* and *Aequorea Victori.*
  ii) Firefly luciferase that utilizes firefly luciferin as Substrate.
  i) Alkaline phosphatase that utilizes DUOLUX™ Chemiluminescent/Fluorescent Substrate for phosphatase.
  ii) Horseradish peroxidase that utilizes DUOLUX™ Chemiluminescent/Fluorescent Substrate for peroxidase, "Chemiluminescent Reaction" means any chemical reaction that produces a photon without an input photon. The reactants may act either catalytically or stoichiometrically. In the case of a catalytic reaction, the catalyst converts a substrate(s) into a product(s) with the concomitant release of a photon. In the case of a stoichiometric reaction, two or more reactants are converted to product(s) and a photon.

"Complementary base pairs" means the purine and pyrimidine bases that pair to form stable hydrogen bonds between two single strand nucleic acid molecules. The usual base pairs are adenine and thymidine, guanine and cytosine, and adenine and uracil. Other base pairs include derivatized variants of these bases, including but not limited to methylated bases, and other purines and pyrimidines including but not limited to inosine.

"Double strand nucleic acid" means two single strand nucleic acid molecules that are non-covalently associated by hydrogen bonding of complementary bases on the two molecules.

"Excitation" means the transfer of energy from a Chemiluminescent Molecule to the Intercalating Dye. Energy transfer from a luminescent molecule to the Intercalating Dye may be through the donation of photons or through Resonance Energy Transfer (RET).

"Hybridization" means the association reaction between two nucleic acid molecules through complementary base pairs to form a double strand nucleic acid.

"Intercalating Dye" means a molecule that binds to double stranded or single stranded nucleic acids between adjacent base pairs. Further, upon intercalation the dye undergoes a change in its electronic configuration such that its absorption and/or emission spectra change. The dye has a very low intrinsic fluorescence when not bound to nucleic acids. The dye has a very large enhancement of fluorescence upon binding to nucleic acids with increases in quantum yields to as high as 0.9. The dye has a very high affinity for nucleic acids and little or no staining of other biopolymers.

"Intercalating Dye Excitation Spectrum" means the range of wavelengths of energy that excites an intercalated dye complexed with double stranded or single stranded nucleic acid to produce a photon at its emission spectrum. The Intercalating Dye Excitation Spectrum overlaps with the emission spectrum of the Chemiluminescent Molecule.

"Intercalating Dye Emission Spectrum" means the wavelengths of photons emitted by intercalated dye complexed with double stranded or single stranded nucleic acid when excited by a light source with a spectrum that overlaps with its maximal excitation wavelength.

"Nucleic acid" means an oligomer or polymer of DNA, RNA or a chimera of both. It includes oligomers or polymers of DNA, RNA or chimeras of both into which analogs of nucleotides have been incorporated. It also includes oligomers and polymers of nucleotide analogs, as would be recognized by one of skill in the art. Examples of nucleotide analogs include nucleotides such as Locked Nucleic Acid (LNA) or Peptide Nucleic Acid (PNA) or other nucleotide analogs that are capable of complementary base-pairing with DNA or RNA, or nucleotide analogs that can be incorporated by enzymes that modify DNA such as telomerases, DNA polymerases, DNA repair enzymes, reverse transcriptases, or DNA and RNA ligases, or other DNA modifying enzymes known to those skilled in the art.

"Probe" means any single strand nucleic acid with a defined sequence of purine and pyrimidine bases, including modifications as would be recognized by one of skill in the art.

"Proximity" means the condition in which different molecules are close by virtue of their association in a stable molecular complex as would be appreciated by one of skill in the art. The molecules may be associated through covalent or non-covalent interactions. It is envisioned that the size of such complexes would be at the level seen in most protein/protein, protein/nucleic acid and nucleic acid/nucleic acid complexes. The proximity of the Chemiluminescent Molecule to nucleic acid would preferably be less than 500 Å. The proximity of the Chemiluminescent Molecule to nucleic acid would more preferably be less than 250 Å. The proximity of the Chemiluminescent Molecule to nucleic acid would most preferably be less than 100 Å. The nucleic acid may have a length much greater than 500 Å.

"Sample" means any mixture of molecules collected from solid, solution or gas that may contain nucleic acid or activity that may modify nucleic acid or inhibitors of said activity.

"Single strand nucleic acid" means an oligomer or polymer of repeating units of phosphate and ribose or deoxyribose joined at the 3' and 5' positions of the sugar rings together with the purine or pyrimidine bases attached at the position of the ribose or deoxyribose ring.

"Solid support" includes any suitable support for a binding reaction and/or any surface to which molecules may be attached through either covalent or non-covalent bonds. This includes, but is not limited to, membranes, plastics, paramagnetic beads, charged paper, nylon, Langmuir-Blodgett films, functionalized glass, germanium, silicon, PTFE, polystyrene, gallium arsenide, gold and silver. Any other material known in the art that is capable of having functional groups such as amino, carboxyl, thiol or hydroxyl incorporated on its surface, is also contemplated. This includes surfaces with any topology, including, but not limited to, flat surfaces, spherical surfaces, grooved surfaces, and cylindrical surfaces e.g., columns. Probes may be attached to specific locations on the surface of a solid support in an addressable format to form an array, also referred to as a "microarray" or as a "biochip."

B. The General Method (the Illustrative Embodiments are not Exhaustive of the Embodiments Disclosed in the Present Invention)

The preferred embodiment of the present invention comprises four molecules: the first is a Chemiluminescent Molecule, the second is a Chemiluminescent Substrate, the third is an Intercalating Dye and the fourth is Nucleic Acids. The absorption spectrum of the Intercalating Dye overlaps with the emission spectrum of the Chemiluminescent Molecule.

In one embodiment, the Chemiluminescent Molecule is linked, covalently or noncovalently, to a single strand nucleic acid complementary to the target sequence; this will be called the "Probe". When the "Sample" nucleic acid is denatured and allowed to reanneal in the presence of the "Probe", the "Probe" and the target sequences in the Sample will form double stranded DNA. This double stranded DNA will in turn associate with the Intercalating Dye. The intercalation of the Intercalating Dye into double stranded will shift the absorption spectrum of the Intercalating Dye to overlap with the emission spectrum of the Chemiluminescent Molecule.

Finally, when the Chemiluminescent Molecule is provided with Chemiluminescent Substrate, it will generate the energy to excite the Intercalated Dye molecules and in turn cause them to emit photons at their emission wavelengths. These photons can be detected/counted. One method to quantitate the light emitted by the dye is to apply a filter that is able to discriminate between light emitted at the lower wavelength from light emitted by the intercalated dye. The efficiency with which energy produced by the Chemiluminescent Molecule is captured by the intercalated Intercalating Dye molecules will depend on the distance between them. The light emitted by the Intercalating Dye is a function the distance between the light source (Chemiluminescent Molecule) and the Intercalating Dye. If Excitation by the Chemiluminescent Molecule occurs by Resonance Energy Transfer then Forster's Equation applies. Forster's Equation states that the transfer of excitation energy between the donor (Chemiluminescent Molecule such as luciferase) and acceptor (Intercalating Dye such as PICOGREEN® quantitation reagent) drops off as the $6^{th}$ power of the distance between the two.

An advantage of the present invention is that no light source aside from the Chemiluminescent Molecule is necessary for detection. Further, the association of the Chemiluminescent Probe with double strand DNA can be measured without physical separation of the target from other double strand nucleic acid, as only double strand DNA with intercalated Intercalating Dye by close physical association with the Chemiluminescent Probe will produce signal over background. This aspect of the invention alleviates the need for washes, a significant advantage as would be recognized by one with skill in the art. Any detector that can discriminate between the shorter and longer spectra wavelengths can be utilized in this assay system. These include, but are not limited to luminometers, fluorimeters, and CCD cameras equipped with a filter to remove shorter wavelengths in the range of that emitted by the Chemiluminescent Molecule.

C. Embodiment Having Probe Directly Labeled with Chemiluminescent Molecule and Sample in Solution FIG. 1 is a schematic representation of a Chemiluminescent Probe being used to quantitate nucleic acid of specific sequence in solution phase. Here the Chemiluminescent Molecule is a luciferase. The luciferase is covalently attached to a ssDNA probe. This Bioluminescent Probe is added to a sample containing target sequence nucleic acid in solution and a nucleic acid stain. Coelenterazine is then added to activate the luciferase. The luciferase excites the nucleic acid intercalated stain that in turn emits a spectrum of light with a maximal wavelength of 520 nm. Light with wavelengths below 500 nm is filtered out. Light with wavelengths greater than 500 nm is permitted to pass to a detector.

Figure 2:
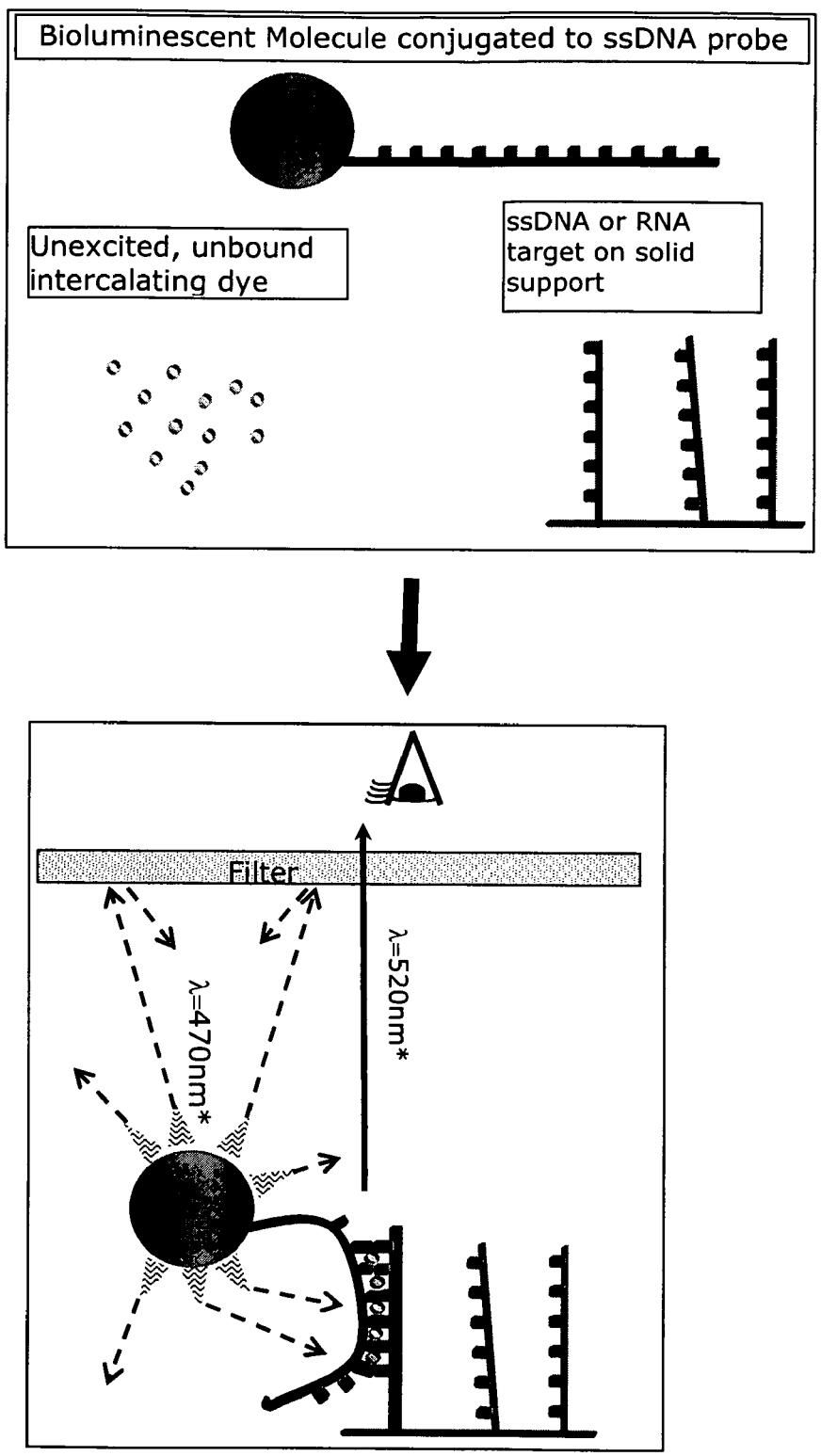
FIG. 2 depicts an embodiment having Probe directly attached to a Chemiluminescent Molecule and Sample is immobilized on Solid Support.

D. Embodiment Having Probe Directly Labeled with Chemiluminescent Molecule and Sample is Immobilized on Solid Support FIG. 2 is a schematic representation of a Chemiluminescent Probe being used to quantitate nucleic acid of specific sequence immobilized on a solid support. Here the Chemiluminescent Molecule is a luciferase. The luciferase is covalently attached to a ssDNA probe. This Bioluminescent Probe is then added to the Sample with target nucleic acid immobilized in a solid support. Nucleic acid stain is present in solution in the Sample. Coelenterazine is then added to activate the luciferase. The luciferase excites the nucleic acid intercalated stain that in turn emits a spectrum of light with a maximal wavelength of 520 nm. Light with wavelengths below 500 nm is filtered out. Light with wavelengths greater than 500 nm is permitted to pass to a detector.

Figure 3:
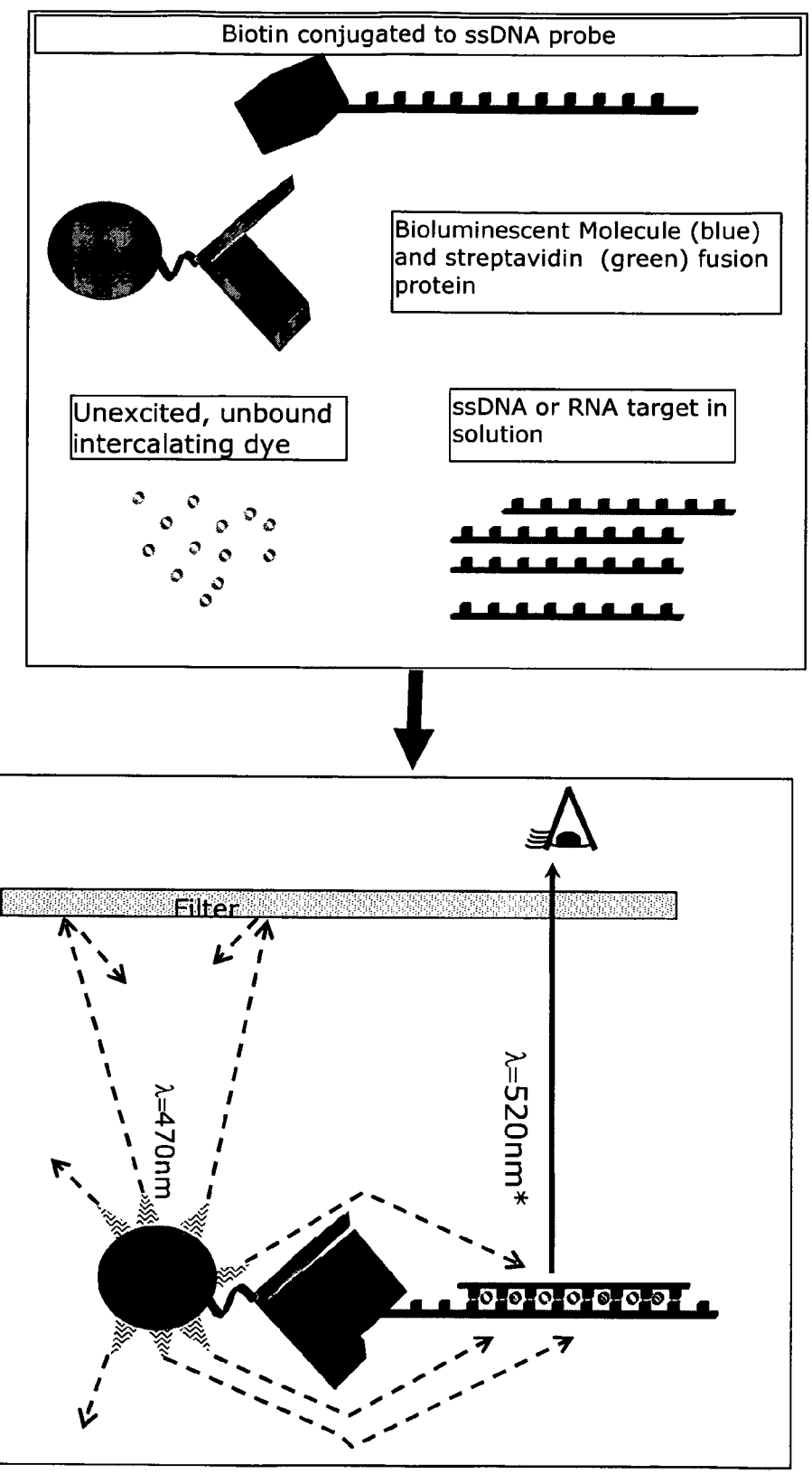
FIG. 3 depicts an embodiment having Probe indirectly attached to a Chemiluminescent Molecule and Sample both are unattached to a Solid Support.

E. Embodiment Having Probe Indirectly Labeled with Chemiluminescent Molecule and Sample in Solution FIG. 3 is a schematic representation of a Chemiluminescent Probe being used to quantitate nucleic of specific sequence in solution phase. Here the Chemiluminescent Molecule is a luciferase. The luciferase is noncovalently conjugated to a biotinylated ssDNA probe through a streptavidin intermediate. Because a single streptavidin molecule may bind four biotin molecules, biotinylated probe DNA, biotinylated luciferase and streptavidin may be mixed in the appropriate ratios to generate a Bioluminescent Probe. The Bioluminescent Probe is added to a sample containing target sequence nucleic acid and a nucleic acid stain. Coelenterazine is added to activate the luciferase. The luciferase then excites the nucleic acid intercalated stain, which in turn emits a spectrum of light with a maximal wavelength of 520 nm. Light with wavelengths below 500 nm is filtered out. Light with wavelengths greater than 500 nm is permitted to pass to a detector.

Figure 4:
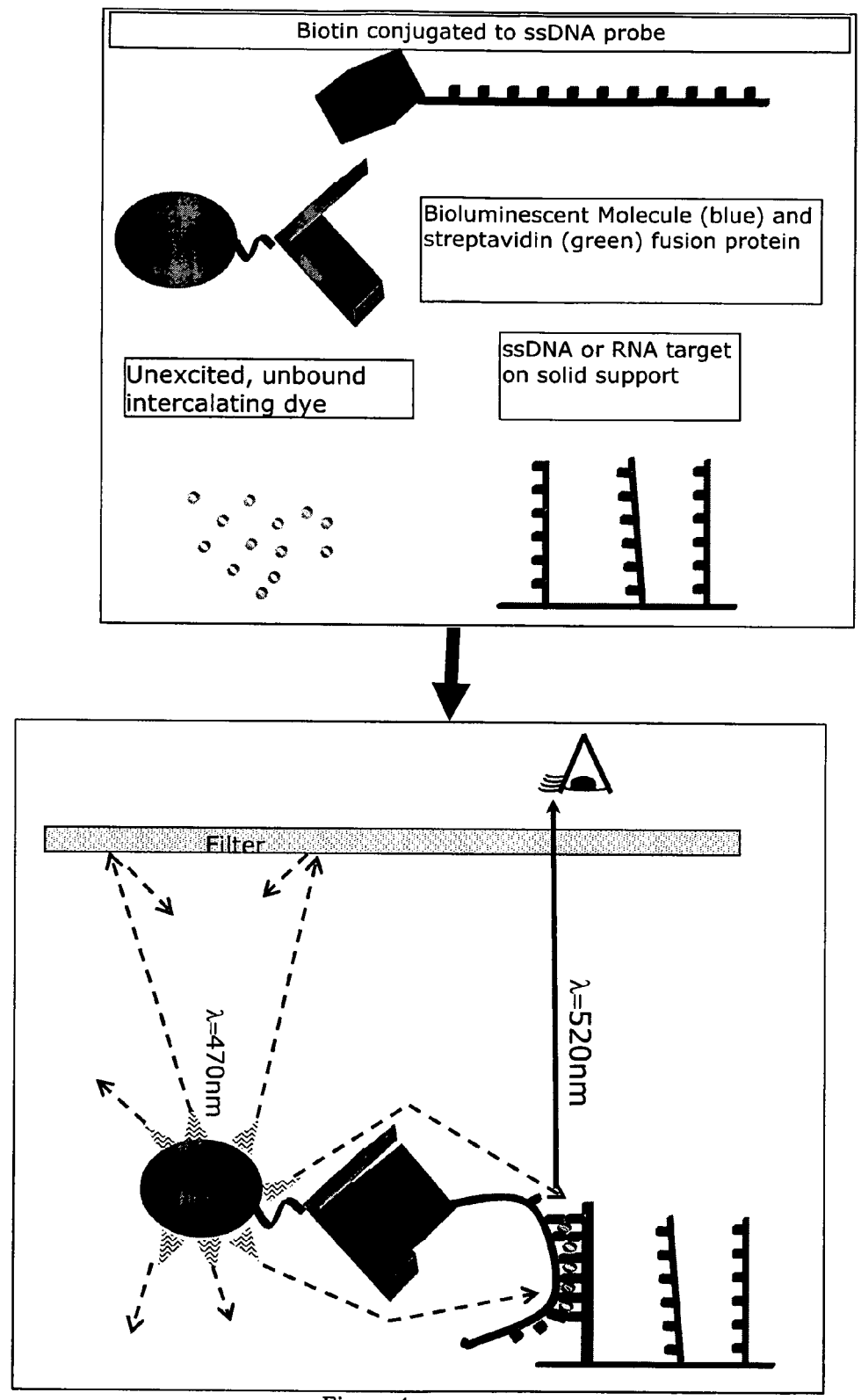
FIG. 4 depicts an embodiment having Probe indirectly attached to a Chemiluminescent Molecule and Sample is immobilized on Solid Support.

F. Embodiment Having Probe Indirectly Labeled with Chemiluminescent Molecule and Sample is Immobilized on Solid Support FIG. 4 is a schematic representation of a Chemiluminescent Probe being used to quantitate nucleic acid of specific sequence immobilized on a solid support. Here the Chemiluminescent Molecule is a luciferase. The luciferase is noncovalently conjugated to a biotinylated ssDNA probe through a streptavidin intermediate. Because a single streptavidin molecule may bind four biotin molecules biotinylated probe DNA, biotinylated luciferase and streptavidin may be mixed in the appropriate ratios to generate a Bioluminescent Probe. This Bioluminescent Probe is then added to the Sample with target nucleic acid immobilized in a solid support. Nucleic acid stain is present in solution in the Sample. Coelenterazine is then added to activate the luciferase. The luciferase excites the nucleic acid intercalated stain, which in turn emits a spectrum of light with a maximal wavelength of 520 nm. Light with wavelengths below 500 nm is filtered out. Light with wavelengths greater than 500 nm is permitted to pass to a detector.

G. Embodiment Having Probe Directly Labeled with Chemiluminescent Molecule, Probe Immobilized on Solid Support and Sample in Solution

H. Uses of the Invention

The invention is a general method for detecting and quantitating target nucleic acid sequences in a heterogeneous mixture of nucleic acids. The detection of nucleic acids is important for many applications, including (but not limited to) diagnostic measurements of nucleic acids in bodily tissues and fluids as would be readily understood by one of skill in the art.

The method serves to monitor the increase or decrease of stainable nuclei acid that is contacted to a Chemiluminescent Molecule. Stainable nucleic acid is any polymer of nucleic acid into which Intercalating Dyes will incorporate as opposed to other biological molecules. Upon binding, these Intercalating Dyes undergo a change in their electronic configuration that makes them fluoresce in the presence of the appropriate excitation wavelength.

This will occur when the mass of stainable nucleic acid that is contacted to the Chemiluminescent molecule is altered. This includes but is not limited to the following:

a. The method measures enzymatic activity that polymerizes the extension of a nascent strand, through the incorporation of nucleotides or nucleotide analogs, of nucleic acid when the extended strand or in the case of duplex its complement are contacted to a Chemiluminescent Molecule and a light responsive intercalating dye is present. Said activity includes but is not limited to RNA polymerases, DNA polymerases and telomerases. The invention also serves to detect inhibitors of the activities thereof;

b. The method measures enzymatic activity that degrades nucleic acid when the nucleic acid is contacted to a Chemiluminescent Molecule and a light responsive intercalating dye is present. Said activity includes but is not limited to RNA exonucleases, RNA endonucleases, DNA exonucleases and DNA endonucleases. The invention also serves to detect inhibitors of the activities thereof;

c. The method measures enzymatic activity that facilitates the attachment or ligation of separate nucleic acid molecules when one of the nucleic acid molecules is contacted to a Chemiluminescent Molecule and a light responsive intercalating dye is present. Said activity includes but is not limited to DNA ligases. The invention also serves to detect inhibitors of the activities thereof;

d. The method measures enzymatic activity that facilitates the recombination of nucleic acid duplex molecules when one of the nucleic acid duplex molecules is contacted to the Chemiluminescent Molecule, a light responsive intercalating dye is present and the mass of the nucleic acid duplex of the recombined product is different than the mass of the nucleic acid duplex of the non-recombined molecule. Said activity includes but is not limited to recombinases and integrases. The invention also serves to detect inhibitors of the activities thereof;

e. The method measures enzymatic activity that facilitates the attachment or ligation of duplex nucleic acid molecules to protein molecules when the protein molecules are contacted to or are a Chemiluminescent Molecule and a light responsive intercalating dye is present. The invention also serves to detect inhibitors of the activities thereof.

All patents and publications referred to herein are expressly incorporated by reference in their entirety. The following examples serve to illustrate certain preferred embodiments and aspects of the present invention and are not to be construed as limiting the scope thereof.

EXAMPLES

Example One

Luciferase activation of DNA intercalated dye is proportional to the DNA present.

Objective:

The objective of this experiment was to determine if the luciferase enzyme of *Gaussia princeps* (gluc) is sufficient to act as an excitation source for a fluorophore that is staining double stranded (ds) DNA. Specifically, the experiment is intended to determine if the gluc which emits light at a peak of 480 nm can excite a dsDNA intercalated nucleic acid stain with an excitation maximum in the range of 495 nm to 500 nm and an emission maximum of approximately 520 nm. This would be done by detecting light from a gluc, fluorescing nucleic acid stain/dsDNA mixture which has had wavelengths below 500 nm filtered out.

Materials and Methods:

The *Gaussia princeps* luciferase was from Avidity LLC (Denver, Colo.). The SYBR Green I nucleic acid stain and the linearized dsDNA ladder were obtained from Invitrogen (Carlsbad, Calif.).

The reactions for the detection of dsDNA were as follows. Dilutions of dsDNA, SYBR GREEN I stain and gluc were made with 50 mM Tris-HCl pH 7.8, 600 mM NaCl, 1 mM EDTA and 20% BPER II (Pierce Biotechnology, Rockford, Ill.). Coelenterazine (Nanolight International, Pinetop, Calif.) was diluted into PBS, 1 mM EDTA. The final concentration of coelenterazine in the reaction was 50 uM.

Figure 5:
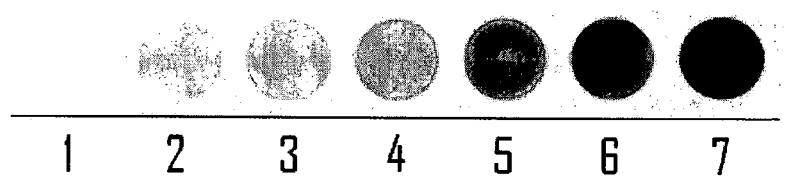
FIG. 5A shows the CCD camera images for reactions described in Example 1 when SYBR GREEN I® stain (formula: [2-[N-(3-dimethylaminopropyl)-N-propylamino]-4-[2,3-dihydro-3-methyl-(benzo-1,3-thiazol-2-yl)-methylidene]-1-phenyl-quinolinium] is the Intercalating Dye. In this experiment the luciferase and SYBR GREEN I® stain concentrations are held constant while the DNA concentration is varied.
FIG. 5B shows the data generated in Example 1 presented as relative intensity per spot.
Figure 5:
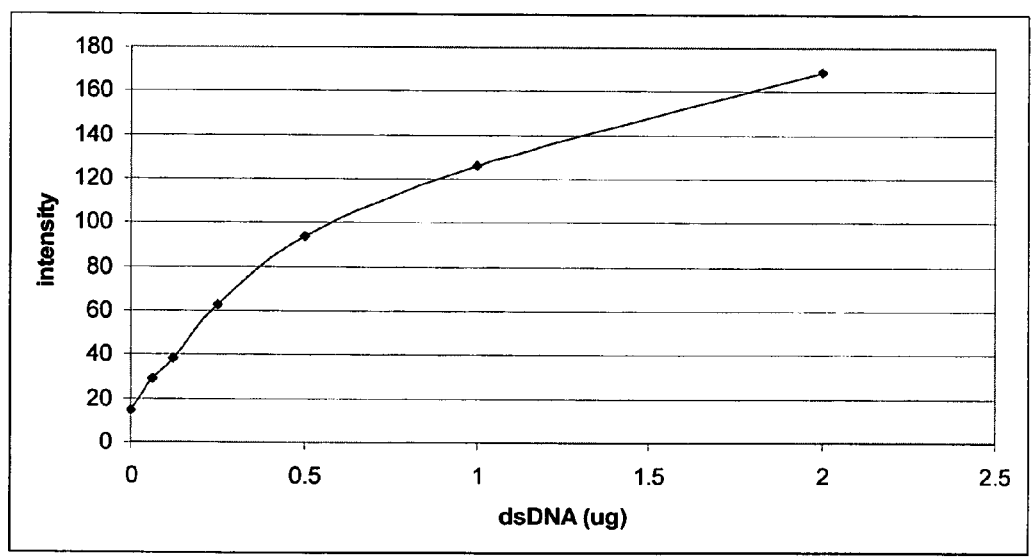

Various amounts of dsDNA were preincubated with 0.78 µl of 200× concentrated SYBR GREEN I stain in a volume of 50 µl A 1× concentration is relative and is that defined by the manufacturer as the standard assay amount for DNA detection. Gluc (50 ng) in 5 µl was added to the prestained dsDNA. The luciferase reaction was initiated by the addition of 100 µl of coelenterazine. The reactions were performed in the wells of a white polystyrene 96 multiwell plate (Evergreen Scientific, Los Angeles, Calif.). Light emitted by the reaction was detected with a CCD camera (Raytest, Straubenhardt, Germany). Quantitative analysis of the images obtained with camera was performed with the AIDA software package (Raytest) that was included with the camera. The capture of light from the reaction by the camera began 10 sec after the reaction was initiated. Light was in 1, 15 min increment (FIG. 5). Discrimination between light emitted by the glue and that emitted by the excited nucleic acid stain/dsDNA duplex was made through the insertion of a filter between the light producing reaction and the aperture of the CCD camera. The aperture setting for the camera was either 0.95 or 11. The filter (Clare Chemical Research, Dolores, Colo.) has been demonstrated to effectively image fluorescing nucleic acid stains that are excited by light wavelengths in the 400 nm to 500 nm range and emit at wavelengths higher than 500 nm when complexed with dsDNA. It does so by significantly filtering out wavelengths lower than 500 nm.

Results:

It was determined that under the conditions used, 50 ng of gluc generated light levels that were within the dynamic range of detection for the CCD camera both with and without the filter. It was also determined that the light generated by this amount of enzyme was as expected, significantly reduced when the filter was used. This level of enzyme was then assayed in the presence of different amounts of dsDNA (FIG. 5). FIG. 5 depicts the light generating reaction performed with 50 ng of glue and coelenterazine in the presence of SYBR Green GREEN I stain and 0 µg, 0.063 µg, 0.125 µg, 0.25 µg, 0.5 µg, 1 µg, and 2 µg of linearized dsDNA (spots 1-7 respectively). Part A shows the CCD camera images for the reactions with filter. Part B shows the same data as relative intensity per spot.

In this experiment it was clearly shown that when both the luciferase enzyme and nucleic acid stain were held constant and the amount of dsDNA was increased, the light produced at longer wavelengths increased proportionally. This demonstrates the ability of gluc to act as an intrinsic light source to activate nucleic acid intercalated dye.

Example 2

Luciferase activation of a DNA intercalated dye is proportional to the amount of dye present.

Objective:

The objective of this experiment was to determine if the luciferase enzyme of *Gaussia princeps* (gluc) is sufficient to act as an excitation source for a fluorophore that is staining double stranded (ds) DNA. Specifically, the experiment is intended to determine if the gluc which emits light at a peak of 480 nm can excite a dsDNA intercalated nucleic acid stain with an excitation maximum in the range of 495 nm to 500 nm and an emission maximum of approximately 520 nm. This would be done by detecting light from a gluc, fluorescing nucleic acid stain/dsDNA mixture which has had wavelengths below 500 nm filtered out.

Figure 6:
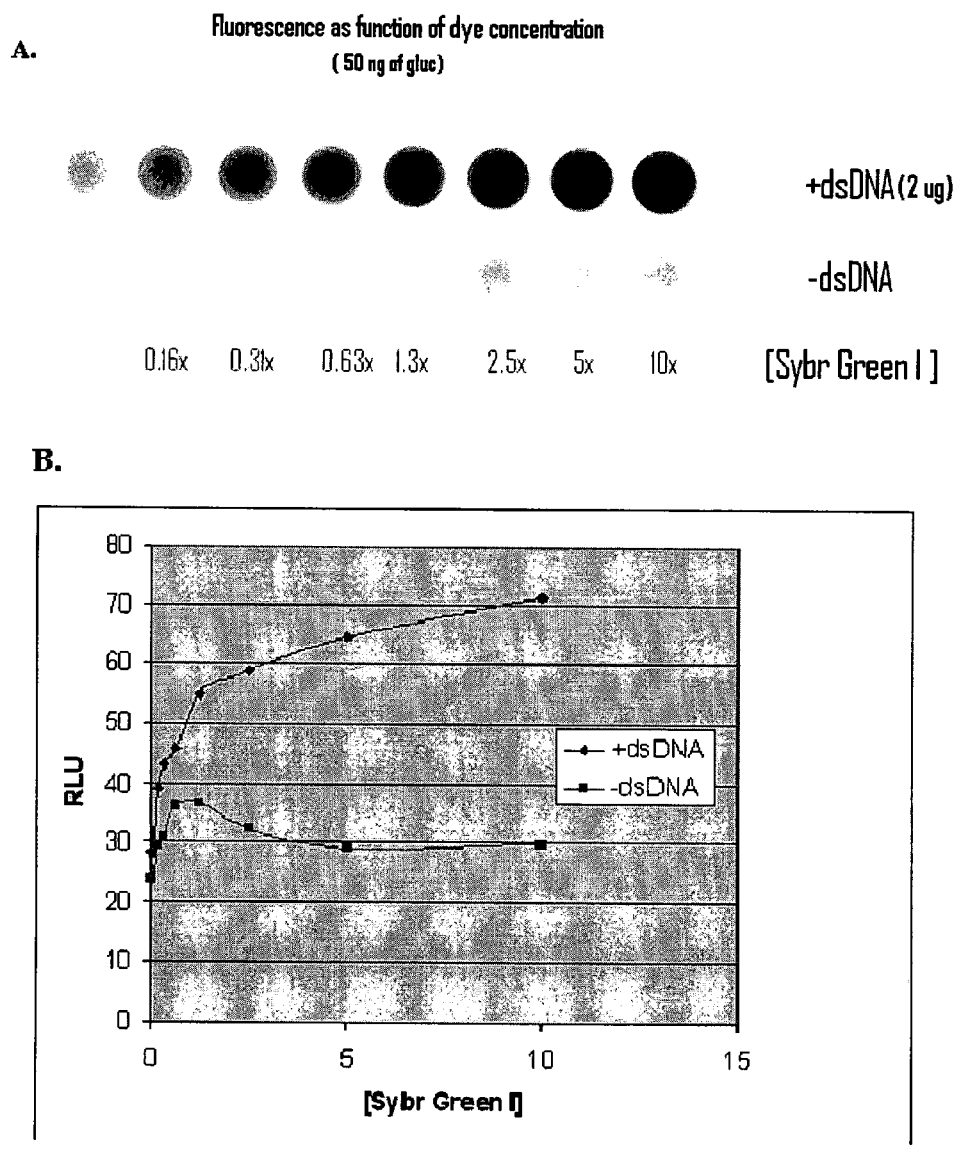
FIG. 6A shows the CCD camera images for reactions described in Example 2 when SYBR GREEN I® stain is the Intercalating Dye. In this experiment the luciferase and DNA concentrations are held constant while the SYBR GREEN I® stain concentration is varied.
FIG. 6B shows the data generated in Example 1 presented as relative intensity per spot when SYBR GREEN I® stain is the Intercalating Dye.

Materials and Methods:

The reactions were performed with the same reagents and under the same conditions as described in Example 1. However, in this experiment the concentrations of dsDNA and gluc are held constant and the concentration of SYBR GREEN I stain is varied (FIG. 6).

dsDNA (2 ug) was preincubated with SYBR GREEN I stain in a volume of 50 µl to final concentrations of 0×, 0.16×, 0.3×, 0.63×, 1.3×, 2.5×, 5×, and 10×. Gluc (50 ng) in 5 µl was added to the prestained dsDNA. The luciferase reaction was initiated by the addition of 100 µl coelenterazine.

The amount of light emitted over 500 nm in each reaction was determined as described in Example 1. The same reactions were also performed in the absence of dsDNA (−dsDNA).

Results:

It was determined that under the conditions used, 50 ng of gluc generated light levels that were within the dynamic range of detection for the CCD camera both with and without the filter. It was also determined that the light generated by this amount of enzyme was as expected, significantly reduced when the filter was used. This level of enzyme was then assayed in the presence of different amounts of SYBR GREEN I stain (FIG. 6). FIG. 6 depicts the light generating reaction performed with 50 ng of glue and coelenterazine in the presence (+dsDNA) or absence (−dsDNA) of linearized dsDNA and SYBR GREEN I stain to final concentrations of 0×, 0.16×, 0.3×, 0.63×, 1.3×, 2.5×, 5×, and 10× (spots 1-8 respectively). Part A shows the CCD camera images for the reactions with filter. Part B shows the same data as relative intensity per spot.

In this experiment it was clearly shown that when both the luciferase enzyme and dsDNA were held constant and the amount of SYBR GREEN I stain was increased, the light produced at longer wavelengths increased proportionally. This demonstrates the ability of gluc to act as an intrinsic light source to activate dsDNA duplex intercalated fluorescing dye.

Example 3

Proximity Dependent Activation of a dsDNA Intercalated Dye

Objective

The purpose of this experiment was to demonstrate the dependence that proximity of the Chemiluminescent Molecule to the nucleic acid intercalated dye has on activation of the dye. In this experiment biotinylated dsDNA target is mixed with biotinylated gluc. In this mixture there is no association of the two species of molecules with one another. Upon addition of increasing amounts of streptavidin the dsDNA and gluc become associated with one another with the streptavidin acting as an intermediate (FIG. 7A). This is due to the tight non-covalent binding of the biotin moieties on the dsDNA and gluc to the four available biotin-binding sites on the streptavidin. As the amount of streptavidin increases the greater the number of molecules of dsDNA that are placed in close proximity to the gluc molecules also increases. If the activation of the intercalated dye is dependent on the close proximity of the gluc to the dye then the amount of fluorescence at longer wavelengths should increase as the amount of streptavidin increases.

Materials and Methods

The reactions were performed with the same reagents and under the same conditions as described in Example 1. However, in this experiment the dsDNA used was made by annealing two complementary synthetic (Sigma-Genosys, The Woodlands, Tex.) oligonucleotides of DNA 85 and 95 nucleotides in length. One of the oligomers (95 nucleotides) was biotinylated at the 5' end. Streptavidin was from Pierce Biotechnology (Rockford, Ill.).

dsDNA (2.5 pmole of biotinylated 5' end per reaction) was preincubated with 0.78 µl of 200× SYBR GREEN I stain in a volume of 50 µl Gluc (50 ng) in 5 µl was added to the prestained dsDNA. Streptavidin in various amounts in 5 µl ddH$_2$O was added to this mix. The mix was incubated 15 min with gentle shaking at room temperature. The luciferase reaction was initiated by the addition of 100 µl of coelenterazine. The amount of light emitted over 500 nm in each reaction was determined as described in Example 1 (FIG. 7B, FIG. 7C).

Results

Figure 7:
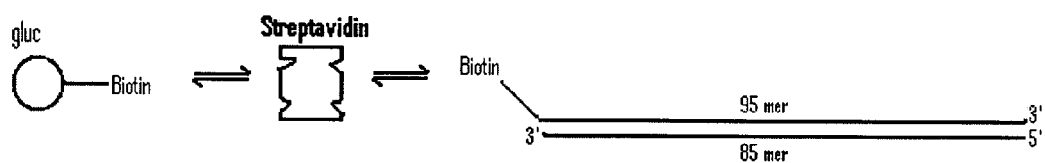
FIG. 7A shows a schematic diagram of the experiment described in Example 3 where the biotinylated gluc is brought into close proximity to the biotinylated DNA duplex by a streptavidin intermediate in the presence of SYBR GREEN I® stain.
FIG. 7B shows the data generated in Example 3 where the biotinylated gluc is brought into close proximity to the biotinylated DNA duplex by a streptavidin intermediate in the presence of SYBR GREEN I® stain.
FIG. 7C shows the data generated in Example 3 presented as relative intensity per spot when SYBR GREEN I® stain is the Intercalating Dye.
Figure 7:
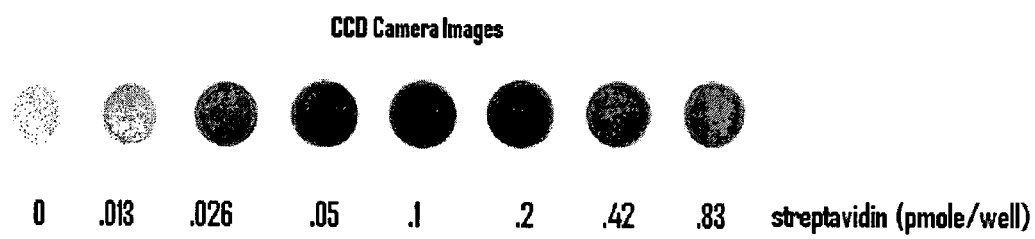
Figure 7:
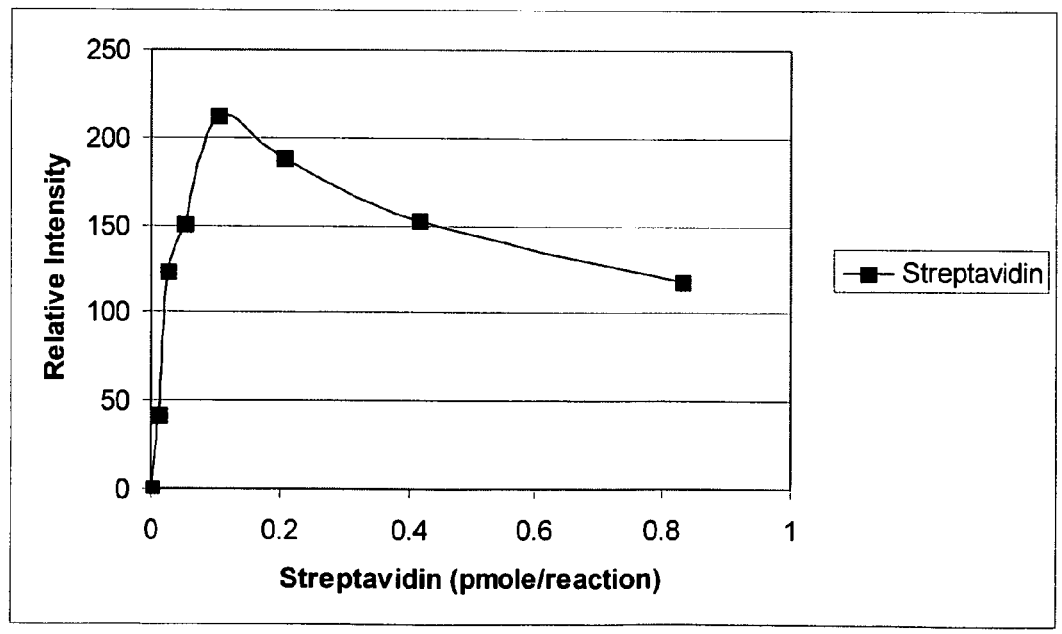

FIG. 7 depicts the light generating reaction performed with 50 ng of biotinylated gluc and coelenterazine in the presence of PICOGREEN® quantitation reagent dye. The DNA target for each reaction was at concentration of 2.5 pmole per biotinylated end per reaction. Streptavidin was present at 0.013 pmole, 0.026 pmole, 0.05 pmole, 0.1 pmole, 0.2 pmole, 0.42, 0.84 pmole (spots 1-8 respectively). Part A shows a schematic diagram of the experimental design. Part B shows the CCD camera images for the reactions with filter. Part C shows the CCD camera images for each reaction assessed as relative intensity per spot.

In this experiment it was shown that the amount of light that can pass through the filter to the CCD camera is directly proportional to the amount of streptavidin that is added. All other components, luciferase, intercalating dye, dsDNA, and coelenterazine are the same in each reaction. The streptavidin serves to bring the Chemiluminescent Molecule (gluc), and stained nucleic acid into a single complex in close proximity to one another. As more streptavidin is added more of the complex is created. The increase in complex is directly proportional the amount of longer wavelength light.

Example 4

Figure 8:
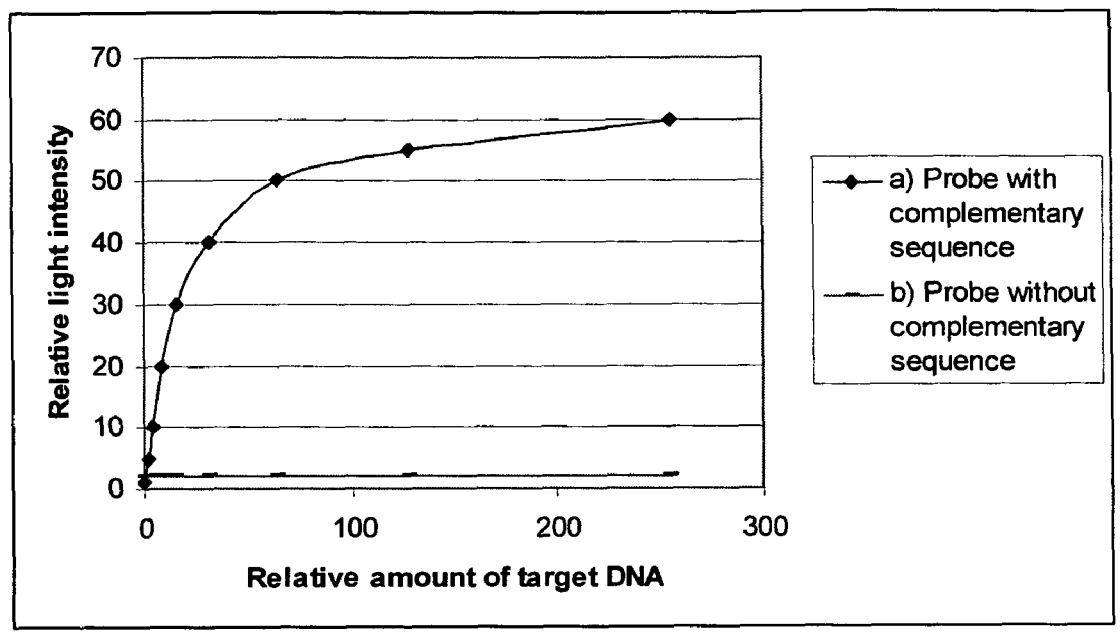
FIG. 8 shows the predicted data from a hypothetical assay using the *Gaussia princeps* luciferase conjugated to a DNA oligomer probe to quantitate DNA of a unique sequence in mixed sample.

FIG. 8 depicts a hypothetical experiment representing a further application of the method. Each data point represents the intensity of a light emitting reaction with the amount of single stranded DNA target increasing in each reaction going from left to right. Gluc/DNA probe, PICOGREEN® quantitation reagent and coelenterazine are held constant. Reactions are with either a) Probe with sequence complementary to the target DNA or b) Probe with sequence not complementary to the target DNA.

The invention claimed is:

1. A method comprising:
   a) providing a sample suspected of containing a nucleic acid of interest, wherein said nucleic acid of interest is covalently or non-covalently attached to a chemiluminescent molecule, wherein said chemiluminescent molecule is selected from the group consisting of blue light luciferases;
   b) contacting the sample with a nucleic acid molecule complementary to the nucleic acid of interest to form a nucleic acid duplex molecule;
   c) contacting the sample with an intercalating dye to generate a dye-bound nucleic acid duplex, wherein the intercalating dye is selected from the group consisting of 2-[N-bis-(3-dimethylaminopropyl)-amino]-4-[2,3-dihydro-3-methyl-(benzo-1,3-thiazol-2-yl)-methylidene]-1-phenyl-quinolinium] and 2-[N-(3-dimethylaminopropyl)-N-propylamino]-4-[2,3-dihydro-3-methyl-(benzo-1,3-thiazol-2-yl)-methylidene]-1-phenyl-quinolinium;
   d) activating said chemiluminescent molecule to produce light, wherein the light excites the dye bound nucleic acid duplex, wherein said activating is initiated by adding a chemiluminescent substrate to the sample, and whereby no light source other than the chemiluminescent molecule is used; and
   e) detecting the light emitted by the excited dye bound nucleic acid duplex, whereby a nucleic acid of interest is detected.

2. A method comprising:
   a) providing a sample suspected of containing a nucleic acid of interest;
   b) contacting the sample with a nucleic acid molecule complementary to the nucleic acid of interest to form a nucleic acid duplex, wherein said nucleic acid complementary to the nucleic acid of interest is covalently or non-covalently attached to a chemiluminescent molecule, wherein said chemiluminescent molecule is selected from the group consisting of blue light luciferases;
   c) contacting the sample with an intercalating dye to generate a dye-bound nucleic acid duplex, wherein the intercalating dye is selected from the group consisting of 2-[N-bis-(3-dimethylaminopropyl)-amino]-4-[2,3-dihydro-3-methyl-(benzo-1,3-thiazol-2-yl)-methylidene]-1-phenyl-quinolinium] and 2-[N-(3-dimethylaminopropyl)-N-propylamino]-4-[2,3-dihydro-3-methyl-(benzo-1,3-thiazol-2-yl)-methylidene]-1-phenyl-quinolinium;
   d) activating said chemiluminescent molecule to produce light, wherein the light excites the dye bound nucleic acid duplex, wherein said activating is initiated by adding a chemiluminescent substrate to the sample, and wherein no light source other than the chemiluminescent molecule is used; and
   e) detecting the light emitted by the intercalating dye, whereby a nucleic acid of interest is detected.

3. The method according to claim 1 or 2, wherein said nucleic acid of interest is selected from the group consisting of DNA, RNA, and derivative thereof.

4. The method according to claim 1 or 2, wherein said nucleic acid molecule complementary to the nucleic acid of interest is selected from the group consisting of DNA, RNA, and derivative thereof.

5. The method according to claim 1 or 2, wherein said chemiluminescent molecule is activated by a luciferin.

6. The method according to claim 1 or 2, wherein at least one of the nucleic acids of interest and the complementary nucleic acid is bound to a solid support.

7. The method according to claim 1 or 2, wherein detecting the light is qualitative.

8. The method according to claim 1 or 2, wherein detecting the light is quantitative.

9. The method according to claim 1 or 2, wherein said chemiluminescent molecule is a blue light luciferase from a system selected from the group consisting of Renilla, Gaussia, Pleuromamma, Aequorea, Obelia, Porichthys, Aristostomias, Odontosyllis, Oplophorus, firefly, bacterial, Cavarnularia, Ptilosarcus, Stylatula, Acanthoptilum, Parazoanthus, Chiroteuthis, Eucleoteuthis, Onychoteuthis, Watasenia; cuttlefish, Sepiolina, Oplophorus, Sergestes, Gnathophausia; Argyropelecus, Yarella, Diaphus, and Neoscopelus systems.

10. The method according to claim 1 or 2, wherein said chemiluminescent molecule is *Gaussia princeps* luciferase.

11. The method of claim 2, wherein said chemiluminescent molecule is associated with said complementary nucleic acid molecule by means selected from the group consisting of covalent and non-covalent interactions.

12. The method of claim 1, wherein said chemiluminescent molecule is associated with said nucleic acid of interest by means selected from the group consisting of covalent and non-covalent interactions.

13. A method comprising:
a) providing a sample suspected of containing a nucleic acid of interest, wherein said nucleic of interest is covalently or non-covalently attached to a *Gaussia luciferase*;
b) contacting the sample with a nucleic acid molecule complementary to the nucleic acid of interest to form a nucleic acid duplex molecule;
c) contacting the sample with an intercalating dye selected from the group consisting of 2-[N-bis-(3-dimethylaminopropyl)-amino]-4-[2,3-dihydro-3-methyl-(benzo-1,3-thiazol-2-yl)-methylidene]-1-phenyl-quinolinium] and 2-[N-(3-dimethylaminopropyl)-N-propylamino]-4-[2,3-dihydro-3-methyl-(benzo-1,3-thiazol-2-yl)-methylidene]-1-phenyl-quinolinium to generate a dye-bound nucleic acid duplex;
d) adding coelenterazine to the sample to activate said *Gaussia luciferase* to produce light that excites the dye-bound nucleic acid duplex; and
e) detecting the light emitted by the excited dye-bound nucleic acid duplex, whereby a nucleic acid of interest is detected.

14. A method comprising:
a) providing a sample suspected of containing a nucleic acid of interest;
b) contacting the sample with a nucleic acid molecule complimentary to the nucleic acid of interest to form a nucleic acid duplex, wherein said nucleic acid complementary to the nucleic acid of interest is covalently or non-covalently attached to a *Gaussia luciferase*;
c) contacting the sample with an intercalating dye selected from the group consisting of 2-[N-bis-(3-dimethylaminopropyl)-amino]-4-[2,3-dihydro-3-methyl-(benzo-1,3-thiazol-2-yl)-methylidene]-1-phenyl-quinolinium] and 2-[N-(3-dimethylaminopropyl)-N-propylamino]-4-[2,3-dihydro-3-methyl-(benzo-1,3-thiazol-2-yl)-methylidene]-1-phenyl-quinolinium to generate a dye-bound nucleic acid duplex;
d) adding coelenterazine to the sample to activate said *Gaussia luciferase* to produce light that excites the dye-bound nucleic acid duplex; and
e) detecting the light emitted by the excited dye-bound nucleic acid duplex, whereby a nucleic acid of interest is detected.

* * * * *